(12) United States Patent
Servoss et al.

(10) Patent No.: US 10,167,315 B2
(45) Date of Patent: Jan. 1, 2019

(54) PEPTOIDS AND METHODS FOR TREATING ALZHEIMER'S DISEASE

(71) Applicants: THE BOARD OF TRUSTEES OF THE UNIVERSITY OF ARKANSAS, Little Rock, AR (US); UNIVERSITY OF SOUTH CAROLINA, Columbia, SC (US)

(72) Inventors: Shannon Servoss, Fayetteville, AR (US); Melissa Moss, Columbia, SC (US); James Phillip Turner, Jr., Fayetteville, AR (US)

(73) Assignees: THE BOARD OF TRUSTEES OF THE UNIVERSITY OF ARKANSAS, Little Rock, AR (US); UNIVERSITY OF SOUTH CAROLINA, Columbia, SC (US)

( * ) Notice: Subject to any disclaimer, the term of this patent is extended or adjusted under 35 U.S.C. 154(b) by 49 days.

(21) Appl. No.: 15/191,925

(22) Filed: Jun. 24, 2016

(65) Prior Publication Data

US 2016/0376311 A1 Dec. 29, 2016

Related U.S. Application Data

(60) Provisional application No. 62/184,057, filed on Jun. 24, 2015.

(51) Int. Cl.
*C07K 7/06* (2006.01)
*A61K 38/00* (2006.01)

(52) U.S. Cl.
CPC ............... *C07K 7/06* (2013.01); *A61K 38/00* (2013.01)

(58) Field of Classification Search
None
See application file for complete search history.

(56) References Cited

U.S. PATENT DOCUMENTS 8,445,632 B2   5/2013   Barron et al.
8,809,275 B2   8/2014   Servoss et al.

FOREIGN PATENT DOCUMENTS

WO   WO 2011/156003   12/2011

OTHER PUBLICATIONS

Luo "inhibiting and Reversing Amyloid-b Peptide (1-40) Fibril Formation with Gramicidin S and Engineered Analogues" Chem Euro 19:17338-17348 (Year: 2013).*
Sengupta "The Role of Amyloid-β Oligomers in Toxicity, Propagation, and Immunotherapy" Ebiomedicine 6:42-49 (Year: 2016).*
Kuperstein "Neurotoxicity of Alzheimer's disease Ab peptides is induced by small changes in the Ab42 to Ab40 ratio" EMBO 29: 3408-3420 (Year: 2010).*
Watson "The amyloid beta face of Alzheimer's disease" accessed from anti-agingfirewalls.com (Year: 2014).*
Adessi, C. et al., "Pharmacological profiles of peptide drug candidates for the treatment of Alzheimer's disease," (2003) J. Biological Chemistry 278(16):13905-13911.
Aileen Funke, S., and Willbold, D. Peptides for Therapy and Diagnosis of Alzheimer's Disease. Curr. Pharm. Des. 2012, 18, 755-767.
Armand, P., et al. NMR Determination of the Major Solution Conformation of a Peptoid Pentamer with Chiral Side Chains. Proc. Natl. Acad. Sci. U. S. A. 1998, 95, 4309-4314.
Churches, Q. I., et al. Naturally Occurring Polyphenolic Inhibitors of Amyloid Beta Aggregation. Bioorganic Med. Chem. Lett. 2014, 24, 3108-3112.
Esler, W. P., et al. Point Substitution in the Central Hydrophobic Cluster of a Human Beta-Amyloid Congener Disrupts Peptide Folding and Abolishes Plaque Competence. Biochemistry 1996, 35, 13914-13921.
Etienne, M. A., et al. Beta-Amyloid Protein Aggregation. Methods Mol. Biol. Clift. Nj 2007, 386, 203-225.
Goldsbury, C., et al. a. Multiple Assembly Pathways Underlie Amyloid-B Fibril Polymorphisms. J. Mol. Biol. 2005, 352, 282-298.
Hamley, I. W., et al. Alignment of a Model Amyloid Peptide Fragment in Bulk and at a Solid Surface. J. Phys. Chem. B 2010, 114, 8244-8254.
Hardy, J., and Selkoe, D. J. The Amyloid Hypothesis of Alzheimer's Disease: Progress and Problems on the Road to Therapeutics. Science 2002, 297, 353-356.
Herrera J., "Peptoid-based therapeutics for Alzheimer's disease," Abstract presented at American Institute of Chemical Engineers 2009 Annual Meeting, Monday, Nov. 9, 2009.
Hudson, S., et al. The Thioflavin T Fluorescence Assay for Amyloid Fibril Detection Can Be Biased by the Presence of Exogenous Compounds. FEBS J. 2009, 276, 5960-5972.
Kirshenbaum, K., et al. Sequence-Specific Polypeptoids: A Diverse Family of Heteropolymers with Stable Secondary Structure. Proc. Natl. Acad. Sci. U. S. A. 1998, 95, 4303-4308.
Laursen, J. S., et al. Cis-Trans Amide Bond Rotamers in β-Peptoids and Peptoids: Evaluation of Stereoelectronic Effects in Backbone and Side Chains. J. Am. Chem. Soc. 2013, 135, 2835-2844.
Lee, S. et al, Small heat shock proteins differentially affect Aβ aggregation and toxicity. Biochem Biophys Res Comm, 2006, vol. 347, 527-533.
Luo, Y., et al. Aβ42-Binding Peptides as Amyloid Aggregation Inhibitors and Detection Ligands. ACS Chemical Neuroscience. 2013. vol. 4. 952-962.

(Continued)

*Primary Examiner* — Adam Weidner
(74) *Attorney, Agent, or Firm* — Andrus Intellectual Property Law, LLP (57) ABSTRACT

Provided herein are peptoids capable of inhibiting or reversing amyloid β (Aβ) fibril or plaque production. The peptoids form a helical structure with three monomers per helical turn and have at least four monomers with a side-chain having an arylalkyl or aryl group. The peptoid may be achiral. Also provided are methods of using the peptoids to inhibit or reverse aggregation of Aβ and methods of treating subjects with Alzheimer's disease (AD) or slowing the progression of AD.

13 Claims, 5 Drawing Sheets

(56) References Cited

OTHER PUBLICATIONS

Luo, Y. et al. Inhibiting and reversing amyloid-b peptide 1-40 fibril formation with gramicidin S and engineered analogues. Chem Eur J. 2013. 19:17338-17348.

Lowe, T. L., et al. Structure-Function Relationships for Inhibitors of Beta-Amyloid Toxicity Containing the Recognition Sequence KLVFF. Biochemistry 2001, 40, 7882-7889.

Miller, S. M., et al. Comparison of the Proteolytic Susceptibilities of Homologous L-Amino Acid, D-Amino Acid, and N-Substituted Glycine Peptide and Peptoid Oligomers. Drug Dev. Res. 1995, 35, 20-32.

Moss, M.A. et al., "The peptide KLVFF-K(6) promotes beta-amyloid(1-40) protofibril growth by association but does not alter protofibril effects on cellular reduction of 3-(4,5-dimethylthiazol-2-yl)-2,5-diphenyltetrazolium bromide (MTT)," (2003) Mol. Pharmacol. (5):1160-1168.

Nilsson, M. R. Techniques to Study Amyloid Fibril Formation in Vitro. Methods 2004, 34, 151-160.

Patch et al., "Versatile Oligo(N-substituted) glycines: The many roles of peptoids in drug discovery;" Pseudo-Peptides in Drug Discovery; Wiley-VCG Verlag (2004).

Patel, D. et al. Attenuation of β-amyloid induced toxicity by sialic acid-conjugated dendrimeric polymers. 2006. Biochimica et Biophysica Acta (BBA). vol. 1760:12. 1802-1809.

Pike, C. J., et al. Amino-Terminal Deletions Enhance Aggregation of beta-Amyloid Peptides in Vitro *. 1995.

Raffi and Aisen, Recent Developments in Alzheimer's Disease Therapeutics. BMC Medicine. 2009. 7:7.

Rajasekhar, K., et al. Rationally Designed Peptidomimetic Modulators of Aβ Toxicity in Alzheimer's Disease. Sci. Rep. 2015, 5, 8139.

Rosenman, D. J., et al. Aβ Monomers Transiently Sample Oligomer and Fibril-like Configurations: Ensemble Characterization Using a Combined MD/NMR Approach. J. Mol. Biol. 2013, 425, 3338-3359.

Sanborn, T. J., et al. Extreme Stability of Helices Formed by Water-Soluble Poly-N-Substituted Glycines (polypeptoids) with Alpha-Chiral Side Chains. Biopolymers 2002, 63, 12-20.

Soto-Ortega, D.D. et al., "Inhibition of amyloid-β aggregation by coumarin analogs can be manipulated by functionalization of the aromatic center," (2011) Bioorganic & Medicinal Chem. 19:2596-2602.

Teplow, D. B. Preparation of Amyloid Beta-Protein for Structural and Functional Studies. Methods Enzymol. 2006, 413, 20-33.

Tjernberg, L. O., et al. Arrest of Beta-Amyloid Fibril Formation by a Pentapeptide Ligand. J. Biol. Chem. 1996, 271, 8545-8548.

Tjernberg, L. O., et al. Controlling Amyloid Beta-Peptide Fibril Formation with Protease-Stable Ligands. J. Biol. Chem. 1997, 272, 12601-12605.

Turner, J.P. et al., "Peptoids: A potential therapeutic agent against Alzheimer's disease," Abstract presented at American Institute of Chemical Engineers 2011 Annual Meeting, Wednesday, Oct. 19, 2011 (Available online Oct. 13, 2011).

Turner, J. P., et al. Rationally Designed Peptoids Modulate Aggregation of Amyloid-Beta 40. ACS Chem. Neurosci. 2014.

Watanabe, K., et al. Inhibitors of Fibril Formation and Cytotoxicity of Beta-Amyloid Peptide Composed of KLVFF Recognition Element and Flexible Hydrophilic Disrupting Element. Biochem. Biophys. Res. Commun. 2002, 290, 121-124.

Wu, C. W., et al. Peptoid Oligomers with Alpha-Chiral, Aromatic Side Chains: Effects of Chain Length on Secondary Structure. J. Am. Chem. Soc. 2001, 123, 2958-2963.

Wu, C. W., et al. Peptoid Oligomers with Alpha-Chiral, Aromatic Side Chains: Sequence Requirements for the Formation of Stable Peptoid Helices. J. Am. Chem. Soc. 2001, 123, 6778-6784.

Wu, J. W., et al. Fibrillar Oligomers Nucleate the Oligomerization of Monomeric Amyloid ?? But Do Not Seed Fibril Formation. J. Biol. Chem. 2010, 285, 6071-6079.

Wu, W., et al. Fibrillar Seeds Alleviate Amyloid-B Cytotoxicity by Omitting Formation of Higher-Molecular-Weight Oligomers. Biochem. Biophys. Res. Commun. 2013, 439, 321-326.

Zuckermann, R.N. et al., "Efficient method for the preparation of peptoids [Oligo(N-substituted glycines)] by submonomer solid-phase synthesis," (1992) J. Am. Chem. Soc. 114:10646-10647.

Office action for U.S. Appl. No. 13/656,198 dated Dec. 27, 2013.

* cited by examiner

|  | JPT1 | JPT1s | JPT1a |
|---|---|---|---|
| % Inhibition | $83.1 \pm 4.8^{\dagger\dagger\dagger}$ | $76.9 \pm 4.8^{\dagger\dagger\dagger}$ | $85.6 \pm 4.8^{\dagger\dagger\dagger}$ |

FIGURE 3

|  | JPT1 | JPT1s | JPT1a |
|---|---|---|---|
| % Inhibition | 46.0 ± 11.4†† | 50.5 ± 9.0†† | 72.6 ± 4.5††,φ |
| Fold-Change | 2.7 ± 0.8 | 2.2 ± 0.3 | <0.5 |

PEPTOIDS AND METHODS FOR TREATING ALZHEIMER'S DISEASE

CROSS-REFERENCE TO RELATED APPLICATIONS

This patent application claims the benefit of priority of U.S. Provisional Patent Application No. 62/184,057, filed Jun. 24, 2016, which is incorporated herein by reference in its entirety.

STATEMENT REGARDING FEDERALLY SPONSORED RESEARCH

This invention was made with United States government support under grant numbers 1P30RR031154-02 and 8P30GM103450-03 from the National Institutes of Health and the National Center for Research Resources, respectively. The United States government has certain rights in this invention.

INTRODUCTION

Alzheimer's disease (AD) is a devastating neurodegenerative disorder, which is clinically characterized by deterioration of memory and cognitive function, progressive impairment of daily living activities, and several neuropsychiatric symptoms. AD is characterized by the buildup of insoluble aggregated amyloid-β protein (Aβ) into plaques that accumulate between the neural cells in the brain. AD is the sixth leading cause of death in the United States and is the only cause of death among the top ten that cannot currently be treated or cured. Researchers have focused on developing small molecules and peptides to prevent Aβ aggregation; however, while some compounds appear promising in vitro, the research has not resulted in a viable therapeutic treatment.

AD is a genetically complex disease and only four genes have been established to either cause early-onset autosomal dominant AD with complete penetrance (APP, PSEN1 and PSEN2) or to increase susceptibility for late-onset AD with partial penetrance (APOE). All four confirmed genes increase the absolute amyloid β protein (Aβ) levels or the ratios of Aβ 42 to Aβ 40, which enhances the aggregation of Aβ into neurotoxic assemblies. The aggregates eventually lead to formation of plaques in the brain and loss of nerve cells.

Currently there are no effective treatments available to stop or even significantly slow the progression of AD. Thus, development of a composition capable of slowing or stopping Aβ aggregation to halt or slow plaque development would be useful.

SUMMARY

Peptoids for inhibiting Aβ aggregation and slowing the progression of AD are provided herein. The peptoids may be capable of reversing Aβ aggregation and plaque formation and thus may reverse or treat AD. The peptoids have the following formula:

H—(NRCH$_2$CO)$_3$—(NACH$_2$CO)$_2$—(NXCH$_2$CO)$_1$—(NACH$_2$CO)$_2$—NH$_2$.

In the formula, the R of the peptoid is an unbranched, saturated or unsaturated, substituted or unsubstituted C$_1$-C$_{10}$ alkyl group; the A of the peptoid comprises an aryl or arylalkyl group, the aryl group may be substituted or unsubstituted and the arylalkyl is unbranched; the X of the peptoid is a branched or unbranched, substituted or unsubstituted, saturated or unsaturated, C$_1$-C$_{10}$ alky, C$_4$-C$_{10}$ aryl, or C$_4$-C$_{10}$ cycloalkyl group; and H is hydrogen, N is nitrogen, C is carbon and O is oxygen. The peptoid may be achiral.

In one aspect, peptoids having monomers in which every third monomer has an arylalkyl R group are provided.

In another aspect, the peptoids are the peptoids provided in Table 1.

In yet another aspect, pharmaceutical compositions comprising the peptoids described herein are provided.

In still another aspect, methods of using the peptoids described herein to inhibit or reverse Aβ aggregation by administering the composition to a subject in need of inhibition of Aβ aggregation.

In still another aspect, methods of using the peptoids described herein to slow the progression of or reverse AD by administering the peptoids to a subject in need of treatment for AD.

BRIEF DESCRIPTION OF THE DRAWINGS

FIG. 3 is a graph and table showing dot blot analysis of aggregation and confirms peptoids JPT1, JPT1a, and JPT1s modulate Aβ40 aggregation and decrease fibrillar aggregate formation. Peptoids were added to 20 μM Aβ40 monomer at concentrations of 0 (control) or 100 μM, aggregation was initiated by agitation and fibrillar aggregates were detected via dot blot analysis employing primary antibody OC as described in the Examples. Peptoids JPT1 and JPT1s extend lag time by 2.67±0.83 and 2.22±0.28 times that of the control, respectively. Peptoid JPT1a decreased lag time extension to <0.42 times that of the control. Normalized values are calculated as a percentage of the control plateau. Parameters are expressed as mean±SEM, n=3. $^{††}$p<0.001 vs. control. $^{Φ}$p<0.01 for JPT1a vs. JPT1 and JPT1s. Data points used for % inhibition measurements are signified with a *.

DETAILED DESCRIPTION

Peptoids for treating Alzheimer's disease (AD), inhibiting the progression of AD and inhibiting or reversing amyloid β protein (Aβ) aggregation are provided herein. AD is a neurodegenerative disease that causes dementia in millions of patients worldwide and for which no effective treatment is currently available. AD is a result of chronic and vast accumulation of a toxic and insoluble Aβ peptide in the brain. The accumulation of Aβ causes loss of synapses, triggers neurofibrillary pathology and neural inflammation and results in neuronal loss. Aβ is an amphipathic peptide and is prone to self-aggregation. The reasons for Aβ accumulation are not clear, but once Aβ fibrils form Aβ plaques they attract further Aβ monomers. Thus once plaques are formed the progression of the disease is inevitable and no treatments currently exist.

Disclosed herein are peptoids (peptidomimetic oligomers) capable of inhibiting or even reversing Aβ fibril and plaque formation and either treating or inhibiting the progression of AD. Peptoids are a class of peptidomimetics that are ideal candidates for use as therapeutic and detection agents due to their increased bioavailability (i.e. resistance to protease degradation) and low immune response. Peptoids have a backbone similar to peptides with the side chains attached to the amide nitrogen rather than the alpha-carbon. This small backbone change imparts peptoid protease resistance as well as an achiral backbone. However, inclusion of chiral side chains within the peptoid sequence allows for the formation of helical secondary structures. Specifically, peptoids containing chiral, aromatic side chains adopt a polyproline type-I like helix, which exhibits a ~6 Å helical pitch and 3 monomers per turn. Peptoid helices are extremely stable and do not denature in up to 8 M urea with temperatures up to 70° C. Peptoids allow for greater bioavailability than peptides since peptoid monomers are linked with an imide bond, which is resistant to proteolytic degradation, and the absence of hydrogen in amide groups in the backbone of the peptoids reduces compound polarity and improves membrane permeability. Use of peptoids may also reduce toxicity associated with peptide breakdown products. The peptoids described herein may be made and used using methods available to those skilled in the art. For example, see Zuckermann et al. Current Opinion in Molecular Therapeutics 11:299-307 (2009) and Ovadia et al. Bioorganic & Medicinal Chemistry 18:580-589 (2010) for information pertaining to the preparation and use of peptoids as therapeutics, the entire contents of which are incorporated herein in their entireties. The Examples below provide methods of making several of the peptoids provided herein.

The peptoids are designed to interact with Aβ and may be capable of reversing or inhibiting Aβ aggregation and plaque formation and thus may reverse or treat AD. The peptoids have the following general formula:

H—(NRCH$_2$CO)$_3$—(NACH$_2$CO)$_2$—(NXCH$_2$CO)$_1$—(NACH$_2$CO)$_2$—NH$_2$.

In the formula, the R of the peptoid is an unbranched, saturated or unsaturated, substituted or unsubstituted C$_1$-C$_{10}$ alkyl group; the A of the peptoid comprises an aryl or arylalkyl group, the aryl group may be substituted or unsubstituted and the arylalkyl is unbranched; the X of the peptoid is a branched or unbranched, substituted or unsubstituted, saturated or unsaturated, C$_1$-C$_{10}$ alkyl, C$_4$-C$_{10}$ aryl, or C$_4$-C$_{10}$ cycloalkyl groups; and H is hydrogen, N is nitrogen, C is carbon and O is oxygen. The peptoid may be achiral. Table 1 shows the structures of three peptoids, namely peptoid JPT1, peptoid JPT1a and peptoid JPT1s which are made and used in the Examples. The Examples demonstrate that JPT1a, an achiral form of peptide JPT1, is capable of inhibiting Aβ aggregation in several different assays and that the aggregation that does occur is structurally distinct as shown by transmission electron microscopy. The structure of JPT1a is shown in Table 1 and includes in the context of the general formula above, R$_1$ of (CH$_2$)$_3$NH$_3^+$, R$_2$ of (CH$_2$)$_2$CH$_3$, R$_3$ of (CH$_2$)$_2$CH$_3$, A is CH$_2$C$_6$H$_5$ and X is (CH$_2$)$_2$CH$_3$. The alkyl portion of each side chain (R, A or X side chains) may have a variable length and the resulting peptoid is expected to inhibit Aβ aggregation and plaque formation.

TABLE 1

Structure, Molecular weight and elution profile of peptoids used herein.

| Structure | MW (Da) | % Elution |
|---|---|---|
| JPT1  | 1130 | 72 |

TABLE 1-continued

Structure, Molecular weight and elution profile of peptoids used herein.

| | Structure | MW (Da) | % Elution |
|---|---|---|---|
| JPT1a | [chemical structure] | 1032 | 73 |
| JPT1s | [chemical structure] | 1130 | 72 |

As used herein, a monomer of the peptoid is a single (—NR—CH$_2$—CO—) group. Suitably, the peptoids are achiral or all the monomers have the same chirality. The peptoid has at least eight monomers as shown in Table 1 and described above. The peptoids shown may also be part of a larger peptoid. Such larger peptoids may include 10, 12, 15, 18, 20, 25, 30 or even 35 monomers. The additional monomers may be included on either end of the active peptoids described herein or may be included on only a single end. In one embodiment, the peptoid has an overall positive charge. In another embodiment, the peptoid is neutral or has a net negative charge. The R groups may be selected from an unbranched, substituted or unsubstituted, saturated or unsaturated, $C_1$-$C_{10}$ alky, $C_4$-$C_{10}$ aryl, $C_4$-$C_{10}$ arylalkyl or $C_4$-$C_{10}$ cycloalkyl groups. In these peptoids, $R_1$ is suitably selected from an unbranched, substituted or unsubstituted $C_1$-$C_{10}$, suitably $C_1$-$C_6$ alkyl, and if substituted the substitution is suitably nitrogen and suitably an amine. $R_1$ may have a positive charge or may be neutral. In the peptoids provided herein $R_1$ is 4-aminobutyl and the first monomer is N-(4-aminobutyl)glycine. Suitably, $R_1$ is a $C_2$-$C_5$ aminoalkyl. Suitably $R_1$ may be 3-aminopropyl, 2-aminoethyl or aminomethyl.

In the peptoids described herein, at least two and as many as two-thirds of the monomers have R groups that are aryl or arylalkyl groups, shown as A in the generic formula above. Suitably the aryl or arylalkyl groups are arranged in the peptoid such that the peptoid has aryl or arylalkyl groups, which are separated by two monomers. The peptoids may form a helical structure with three monomers per helical turn of the peptoid such that the aryl or arylalkyl groups are stacked on one side of the helix in the peptoids. In some embodiments, the aryl or arylalkyl groups are spaced such that every third monomer in the peptoid is an aryl or arylalkyl. In other embodiments, one third or up to two thirds of the monomers have aryl or arylalkyl groups such that one or two out of every three R groups in the peptoid are aryl or arylalkyl groups. Suitably, the aryl or aryl alkyl groups are 1-phenylmethyl as shown in Table 1. Suitably additional aryl or arylalkyl groups may be used such as a phenyl, phenylethyl, phenylpropyl, phenylbutyl. The aryl portion of the groups may include between 6 and 30 carbons. The arylalkyl may be unbranched, substituted or unsubstituted and the alkyl portion may be saturated or unsaturated. Suitably the aryl or arylalkyl groups are unsubstituted or substituted with N, S or O.

The remaining R groups may be unbranched, substituted or unsubstituted, saturated or unsaturated $C_1$-$C_{10}$ alky, or $C_4$-$C_{10}$ cycloalkyl groups. The X group is suitably a branched or unbranched, substituted or unsubstituted, saturated or unsaturated, $C_1$-$C_{10}$ alky, $C_4$-$C_{10}$ aryl, $C_4$-$C_{10}$ arylalkyl or $C_4$-$C_{10}$ cycloalkyl groups. The R groups and the X group are independently selected from unbranched, substituted or unsubstituted, saturated or unsaturated, $C_1$-$C_{10}$ alkyl, aryl, heteroaryl, arylalkyl, cyclic, heterocyclic groups. Suitably, the peptoid has at least eight monomers, similar to those shown in Table 1, in which $R_2$ and $R_3$ and X are independently selected from 4-aminobutyl, 3-aminopropyl, 2-aminoethyl, or aminomethyl, pentyl, butyl, propyl, ethyl, methyl. The R groups may be achiral as well.

Without being limited by theory, the benzene rings of the aryl groups are believed to interact with Aβ and block formation or growth of β-sheet aggregates. Thus, a peptoid with side chains having benzene rings in every third position will form a helical structure with one face of the helix capable of interacting with Aβ to block aggregation or even reverse aggregation. Suitably, a peptoid with monomers having two aryl side chains followed by a third non-aryl containing monomer would provide a peptoid having two faces capable of interacting with Aβ and blocking Aβ aggregate formation or growth.

Suitably, the peptoid is capable of inhibiting aggregation of Aβ by at least 75% in the thioflavin T assay as compared to a control untreated sample. Suitably, the peptoid is capable of inhibiting aggregation of Aβ by at least 80%, 85%, 90%, 93%, 95%, 97%, 98%, 99% or more. Suitably, the peptoid is able to accomplish the levels of inhibition dictated when added at an equimolar amount with the Aβ, or when added in excess, for example at a ratio of 0.25, 0.5, 0.75. 1, 1.5, 2, 2.5, 3, 5, 7 or even 10 fold molar excess as compared to the Aβ. The peptoids may be capable of inhibiting Aβ aggregation by at least 10% as measured by a decrease in antibody binding to aggregated Aβ as compared to a control in which the Aβ monomers are allowed to aggregate alone. The peptoids described herein are capable of inhibiting aggregation and in particular fibrillar aggregation by 12%, 14%, 16%, 18%, 20% or even more.

The term "alkyl group" is intended to mean a group of atoms derived from an alkane by the removal of one hydrogen atom. Thus, the term includes straight or branched chain alkyl moieties including, for example, methyl, ethyl, propyl, isopropyl, butyl, tert-butyl, pentyl, hexyl, and the like. Preferred alkyl groups contain from 1 to about 14 carbon atoms ($C_{1-14}$ alkyl).

The term "aryl group" is intended to mean a group derived from an aromatic hydrocarbon by removal of a hydrogen from the aromatic system. Preferred aryl groups contain phenyl or substituted phenyl groups. Thus, the term "aryl" includes an aromatic carbocyclic radical having a single ring or two condensed rings. This term includes, for example, phenyl or naphthyl.

The term "heteroaryl" refers to aromatic ring systems of five or more atoms (e.g., five to ten atoms) of which at least one atom is selected from O, N and S, and includes for example furanyl, thiophenyl, pyridyl, indolyl, quinolyl and the like.

"Substituted" means that one or more of the hydrogen atoms bonded to carbon atoms in the chain or ring have been replaced with other substituents. Suitable substituents include monovalent hydrocarbon groups including alkyl groups such as methyl groups and monovalent heterogeneous groups including alkoxy groups such as methoxy groups or amines. "Unsubstituted" means that the carbon chain or ring contains no other substituents other than carbon and hydrogen.

"Branched" means that the carbon chain is not simply a linear chain. "Unbranched" means that the carbon chain is a linear carbon chain.

"Saturated" means that the carbon chain or ring does not contain any double or triple bonds. "Unsaturated" means that the carbon chain or ring contains at least one double bond. An unsaturated carbon chain or ring may include more than one double bond.

The term "acyl or acetyl group" is intended to mean a group having the formula RCO—, wherein R is an alkyl group or an aryl group.

The term "alkenyl" refers to a straight or branched chain alkyl moiety having two or more carbon atoms (e.g., two to six carbon atoms, $C_{2-6}$ alkenyl) and having in addition one double bond of either E or Z stereochemistry where applicable. This term would include, for example, vinyl, 1-propenyl, 1- and 2-butenyl, 2-methyl-2-propenyl, etc.

The term "cycloalkyl" refers to a saturated alicyclic moiety having three or more carbon atoms (e.g., from three to six carbon atoms) and which may be optionally benzofused at any available position. This term includes, for example, cyclopropyl, cyclobutyl, cyclopentyl, cyclohexyl, indanyl and tetrahydronaphthyl.

The term "heterocycloalkyl" refers to a saturated heterocyclic moiety having three or more carbon atoms (e.g., from three to six carbon atoms) and one or more heteroatom from the group N, O, S (or oxidized versions thereof) and which may be optionally benzofused at any available position. This term includes, for example, azetidinyl, pyrrolidinyl, tetrahydrofuranyl, piperidinyl, indolinyl and tetrahydroquinolinyl.

The term "cycloalkenyl" refers to an alicyclic moiety having three or more carbon atoms (e.g., from three to six carbon atoms) and having in addition one double bond. This term includes, for example, cyclopentenyl or cyclohexenyl.

The term "heterocycloalkenyl" refers to an alicyclic moiety having from three to six carbon atoms and one or more heteroatoms from the group N, O, S (or oxides thereof) and having in addition one double bond. This term includes, for example, dihydropyranyl.

The term "arylalkyl" refers to an alkyl group as defined above substituted with one or more aryl group as defined above. Suitably, the arylalkyl group is an alkyl group substituted with one aryl group such as a phenylethyl or phenylmethyl group.

The term "halogen" means a halogen of the periodic table, such as fluorine, chlorine, bromine, or iodine.

The term "optionally substituted" means optionally substituted with one or more of the aforementioned groups (e.g., alkyl, aryl, heteroaryl, acyl, alkenyl, cycloalkyl, heterocycloalkyl, cycloalkenyl, heterocycloalkenyl, nitrogen, oxygen, sulfur or halogen) at any available position or positions.

Methods of making the compounds described herein are provided in the Examples. The compounds may be synthesized using conventional chemical technologies available to those skilled in the art. Salts of the compounds described herein are also provided. Suitably, the salts are pharmaceutically acceptable. Acceptable salts of the compounds include, but are not limited to, hydrochloride, hydrobromide, hydroiodide, nitrate, sulfate, bisulfate, phosphate, acid phosphate.

The compounds may be used to make pharmaceutical compositions. Pharmaceutical compositions comprising the peptoids described above and a pharmaceutically acceptable carrier are provided. A pharmaceutically acceptable carrier is any carrier suitable for in vivo administration. Examples of pharmaceutically acceptable carriers suitable for use in the composition include, but are not limited to, water, buffered solutions, glucose solutions, oil-based or bacterial culture fluids. Additional components of the compositions may suitably include, for example, excipients such as stabilizers, preservatives, diluents, emulsifiers and lubricants. Examples of pharmaceutically acceptable carriers or diluents include stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer). Especially when such stabilizers are added to the compositions, the composition is suitable for freeze-drying or spray-drying. The composition may also be emulsified.

The peptoids provided herein may be used to make compositions capable of inhibiting Aβ aggregation both in vitro and in vivo and are capable of slowing the progression of AD in subjects suffering therefrom. In the methods, compositions comprising the peptoids described herein are administered to the subject in need of treatment. Suitably, the compositions are formulated and administered such that the peptoids are able to cross the blood-brain barrier. Suitably, the peptoids provided herein are able to treat or slow the progression of AD. Suitably, the peptoids provided herein are capable of reversing the progression of AD. Suitably, the peptoids are capable of breaking down or reversing aggregation of Aβ. Suitably, the subjects are mammals, more suitably, humans.

Treatment of AD includes but is not limited to, prophylaxis of symptoms or indicators of the condition, reduction in disease severity or progression, or reversal, reduction or slowing in disease progression as compared to an untreated subject. The compositions described herein may be used to treat subjects in need of treatment for AD and may be used in combination with a second composition capable of inhibiting or slowing the progression of AD. The two compositions used together to treat a subject may be administered simultaneously or concomitantly or one before the other in any order. The two compositions may be administered such that one is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks or more.

The compositions described herein may be administered by any means known to those skilled in the art, including, but not limited to, oral, topical, intranasal, intraperitoneal, parenteral, intravenous, intramuscular, subcutaneous, intrathecal, transcutaneous, nasopharyngeal, or via transmucosal absorption. Thus the compositions may be formulated as an ingestable, injectable, intranasal, topical or suppository formulation. The compositions may also be delivered with in a liposomal or time-release vehicle. Suitably, the compositions are administered such that they are delivered or are able to cross the blood-brain barrier. Administration of the compositions to a subject appears to exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the composition or compositions being administered, the disease to be treated or inhibited, the condition of the subject, and other relevant medical factors that may modify the activity of the composition or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the composition of the invention and of a known agent, such as by means of an appropriate conventional pharmacological or prophylactic protocol.

The maximal dosage for a subject is the highest dosage that does not cause undesirable or intolerable side effects. The number of variables in regard to an individual prophylactic or treatment regimen is large, and a considerable range of doses is expected. The route of administration will also impact the dosage requirements. It is anticipated that dosages of the composition will inhibit progression of the condition by at least 10%, 20%, 30%, 40%, 50%, 60%, 70%, 80%, 90% or 100% compared to pre-treatment symptoms or progression of the disease if left untreated. It is specifically contemplated that pharmaceutical preparations and compositions may palliate or alleviate symptoms of the disease without providing a cure, or, in some embodiments, may be used to stop progression of the disease or disorder and in some cases may even reverse progression.

Suitable effective dosage amounts for administering the compositions may be determined by those of skill in the art, but typically range from about 1 microgram to about 100,000 micrograms per kilogram of body weight weekly, although they are typically about 1,000 micrograms or less per kilogram of body weight weekly. In some embodiments, the effective dosage amount ranges from about 10 to about 10,000 micrograms per kilogram of body weight weekly. In another embodiment, the effective dosage amount ranges from about 50 to about 5,000 micrograms per kilogram of body weight weekly. In another embodiment, the effective dosage amount ranges from about 75 to about 1,000 micrograms per kilogram of body weight weekly. The effective dosage amounts described herein refer to total amounts administered, that is, if more than one composition is administered, the effective dosage amounts correspond to the total amount administered. The composition can be administered as a single dose or as divided doses. For example, the composition may be administered two or more times separated by 4 hours, 6 hours, 8 hours, 12 hours, a day, two days, three days, four days, one week, two weeks, or by three or more weeks.

An effective amount or a therapeutically effective amount as used herein means the amount of a composition that, when administered to a subject for treating a state, disorder or condition is sufficient to effect a treatment (as defined above). The therapeutically effective amount will vary depending on the composition, formulation or composition, the disease and its severity and the age, weight, physical condition and responsiveness of the subject to be treated.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

Examples

1. Introduction

JPT1 (Table 1) was designed to mimic the peptide KLVFF and exhibits a helical secondary structure in both methanol and water (indicated by circular dichroism) as a result of the presence of chiral, aromatic (F-like) and aliphatic (I-like) side chains. It contains adjacent aromatic side chains with ~6 Å spacing on two faces of the helix. A similar ~6 Å spacing is observed between contiguous backbone carbons within β-sheets, the secondary structure adopted upon aggregation of Aβ. This congruence was incorporated within the peptoid design to facilitate pi-pi stacking between the aromatic groups of the peptoid and adjacent F residues within the hydrophobic core of Aβ. Previous studies of JPT1 showed that the peptoid is able to effectively modulate Aβ40 aggregation by reducing the overall number of β-sheet containing aggregates formed at equilibrium. Turner et al. ACS Chem Neurosci 5: 552-558 (2014). These results indicate that protease-resistant peptoid-based mimics of KLVFF may hold therapeutic promise for AD.

To test the validity of this hypothesis, two additional novel peptoid-based mimics of KLVFF have been designed that alter the placement of aromatic groups (JPT1s) and remove side chain chirality (i.e., peptoid helicity) (JPT1a). The ability of these peptoid sequences to modulate Aβ40 aggregation was compared to that of JPT1. The results presented here show that these new peptoid sequences both modulate Aβ40 aggregation, with slightly different efficacy than JPT1. However, JPT1a, which lacks side chain chirality, induces an altered Aβ aggregate morphology compared to JPT1 and JPT1s.

2. Experimental Procedures 2.1. Materials (N)—(S)-sec-butylamine (chiral I-like side chain), (S)—(−)-α-methylbenzylamine (chiral F-like side chain), benzylamine (achiral F-like side chain), propylamine (achiral I-like side chain), piperidine, and thioflavin T (ThT) were purchased from Sigma-Aldrich (St. Louis, Mo.). tert-Butyl N-(4-aminobutyl) carbate (Boc protected K-like side chain) was purchased from CNH Technologies, Inc. (Woburn, Mass.). MBHA rink amide resin was purchased from NovaBiochem (Gibbstown, N.J.). Aβ40 was purchased from Anaspec, Inc. (Freemont, Calif.). Primary antibody OC was purchased from EMD Millipore (Billerica, Mass.). Alkaline phosphatase-conjugated anti-rabbit IgG was purchased from Thermo Scientific (Rockford, Ill.). All other reagents used during synthesis, purification, and sample preparation were purchased from VWR or Fisher. All chemicals were used without further modification unless otherwise indicated.

2.2. Peptoid Synthesis and Purification

Peptoids were synthesized via a two-step process of Zuckermann et al., Am Chem Soc 114:10646-10647 (1992), using an Applied Biosystems 433A automated peptide synthesizer (Carlsband, Calif.) that was refurbished from a 431A synthesizer. Rink amide resin was swelled with dimethylformamide (DMF), and the Fmoc protecting group was removed using 20% piperidine in DMF. The secondary amine was acylated by adding 1.2 M bromoacetic acid in DMF and diisopropylcarbodiimide at a ratio of 5.3:1 and vortexing for 60 min. Side chain amines were added to the resin via an $S_N 2$ reaction mechanism. The peptoid was removed from the resin by bathing it in a cleavage cocktail containing 95% trifluoroacetic acid (TFA), 2.5% triisoproylsilane, and 2.5% water for 5 min. The acid was removed using a Heidolph Laborota 4001 rotating evaporator (Elk Grove Village, Ill.), and the peptoid was diluted to a concentration of ~3 mg mL$^{-1}$ in a 35:65 solution of acetonitrile-water. Peptoids were purified using a Waters Delta 600 preparative high performance liquid chromatography unit (HPLC; Milford, Mass.) with a Duragel G C18 150×20 mm column (Peeke Scientific, Novato, Calif.). Gradients were run at ~1% per minute with 5-95% solvent B in A (solvent A: water, 5% acetonitrile, 0.1% TFA; solvent B: acetonitrile, 5% water, 0.1% TFA). Peptoids were confirmed to be >98% pure via analytical HPLC (Waters 2695 Separations Module) equipped with a Duragel G C18 150×2.1 mm column (Peeke Scientific) using a linear gradient of 5 to 95% solvent D in C (solvent C: water, 0.1% TFA; solvent D: acetonitrile, 0.1% TFA) over 30 min (data not shown). MALDI-TOF mass spectrometry was used to confirm that the purified peptoid mass matched the theoretical mass (data not shown). Purified peptoid solutions were dried to powder using a Labconco lyophilizer (Kansas City, Mo.) and stored at −20° C.

2.3. Circular Dichroism

Circular dichroism (CD) spectrometry analysis was performed using an AVIV-215 circular dichroism spectrometer (AVIV Biomedical, Inc., Lakewood, N.J.) at room temperature with a scanning speed of 6 nm min$^{-1}$. Peptoids were measured in pure methanol at a concentration of 120 μM. Each CD spectra is the cumulative average of 3 scans.

2.4. Preparation of Aβ Protein Solution

Aβ40 was dissolved in cold 1,1,1,3,3-hexafluoro-2-propanol (HFIP) to create a 1 mM solution and was incubated on ice for 60 min. After incubation, the solution was aliquoted into individual silicon-coated vials, and HFIP was allowed to evaporate overnight at room temperature, resulting in a thin protein film that was stored with desiccant at −80° C. until use. Prior to experimentation, protein films were rehydrated with 5 mM NaOH on ice for 5 min, and then 40 mM Tris-HCl (pH 8.0) was added for 10 min on ice for a final concentration of 250 μM NaOH.

2.5. Aβ40 Aggregation Assay

Aggregation assays were performed with 20 μM rehydrated Aβ40 in 40 mM Tris-HCl (pH 8.0) and 150 mM NaCl. Peptoids were dissolved in DMSO and added at 100 μM such that the final DMSO concentration was 5% (v/v). Assays were performed at 25° C. with agitation on an orbital shaker at 800 rpm.

2.6. ThT Fluorescence

To monitor aggregation using ThT, an aliquot of the aggregation reaction was taken at varying time points and combined with 12.5 μM ThT at a 5:1 molar ratio (ThT:Aβ). Samples were mixed for 8 s and then scanned with a Shimazdu RF-150 mini fluorometer (excitation at 440±10 nm and emission at 490±10 nm) using an average scan time of 4 s. ThT fluorescence with background (ThT alone) subtraction was normalized to the fluorescence detected at equilibrium within the control reaction, and results were plotted against time. Lag time was noted for both the control and peptoid reactions as the time point before a significant increase in fluorescence was observed (>5% of the plateau). The fold-change in the lag time was calculated as the ratio of the lag time observed in the presence of peptoid to that of the control. The equilibrium plateau was determined for both the control and peptoid reactions, and percent inhibition was calculated as the percentage decrease of the equilibrium plateau observed in the presence of peptoid relative to the control.

2.7. Dot Blot

In parallel with ThT fluorescence, aggregation assays were also assessed by dot blot analysis. Samples (2 μL) were spotted onto 0.1 μm nitrocellulose membrane (GE Healthcare, Pittsburg, Pa.) and immediately blocked with 5% skim milk in Tris buffered saline containing 0.2% Tween20 (TBS-T) at 4° C. overnight. Membranes were washed three times with TBS-T and incubated with Aβ fibril specific OC antibody (1:5000 dilution) for 1 h at room temperature with gentle agitation. Membranes were again washed three times with TBS-T. Protein detection for bound OC antibody was performed by binding alkaline phosphatase-conjugated anti-rabbit IgG (1:3000 dilution) for 1 h at room temperature with gentle agitation. Dot blots were developed using nitro blue tetrazolium and 5-bromo-4-chloro-3-indolyl phosphate in TBS-T/$MgCl_2$ until no precipitate was observed. The developing reaction was halted using a 10% acetic acid solution. Dot blots were immediately imaged using a Canon CanoScan 9000F (Tokyo, Japan). Images were analyzed with ImageJ software using the gel lane analysis tool. Dot density was normalized to the density detected at equilibrium for the control and plotted against time. The fold-change in lag time and percent inhibition were assessed as described for ThT fluorescence.

2.8. Transmission Electron Microscopy

Monomer aggregation reactions were gridded for transmission electron microscopy (TEM) at 255 min, a time by which the control reaction had reached plateau as observed by ThT fluorescence. A 3 μL sample was placed onto a wax substrate, and a 300 square mesh formvar-carbon supported nickel grid (Electron Microscopy Sciences, Hatfield, Pa.) was inverted onto the sample. After 1 min, the sample was wicked away from the bottom side of the grid using a piece of filter paper. A 3 μL sample of 2% uranyl acetate was then placed onto the wax substrate, and the grid was inverted onto the solution for a period of 45 s. Excess stain was wicked away with a piece of filter paper, and the grids were allowed to dry for a period of 24 h. Imaging was performed using a JEOL-1011 transmission electron microscope (JEOL Ltd., Tokyo, Japan) with an accelerating voltage of 110 kV. Blinded observation of samples with random selection of grid areas was implemented to reduce bias during imaging. Images are the representative of 3 repeated experiments and 3 random sections of the grids.

2.9. Nile Red Spectroscopy

To monitor peptoid-induced changes in aggregate surface hydrophobicity, which are indicative of changes in aggregate conformation, an aliquot of the aggregation reaction was taken from the equilibrium plateau and combined with 200 μM Nile Red (Life Technologies, Carlsbad, Calif.) at a 10:1 molar ratio (Nile Red:Aβ). Samples were scanned using a PerkinElmer LS 45 Luminescence Spectrometer (excitation at 550 nm and emission from 580-700 nm), and the integrated area under the curve (IAUC) was calculated from 580-700 nm. The IAUC was blank (Nile Red, peptoid) subtracted and normalized to Nile Red measurements performed for the control reaction.

2.10. Statistical Analysis

Data were analyzed using XLSTAT Statistical Software for Microsoft Excel (Addinsoft, New York, N.Y.). Differences in percent inhibition were assessed using a one-way analysis of variance (ANOVA) for ThT fluorescence and dot blot analysis. Dunnett's post-test was used to identify groups with means significantly different from control.

3. Results

3.1. Peptoid Sequence, Rationale, and Characterization

Figure 1:
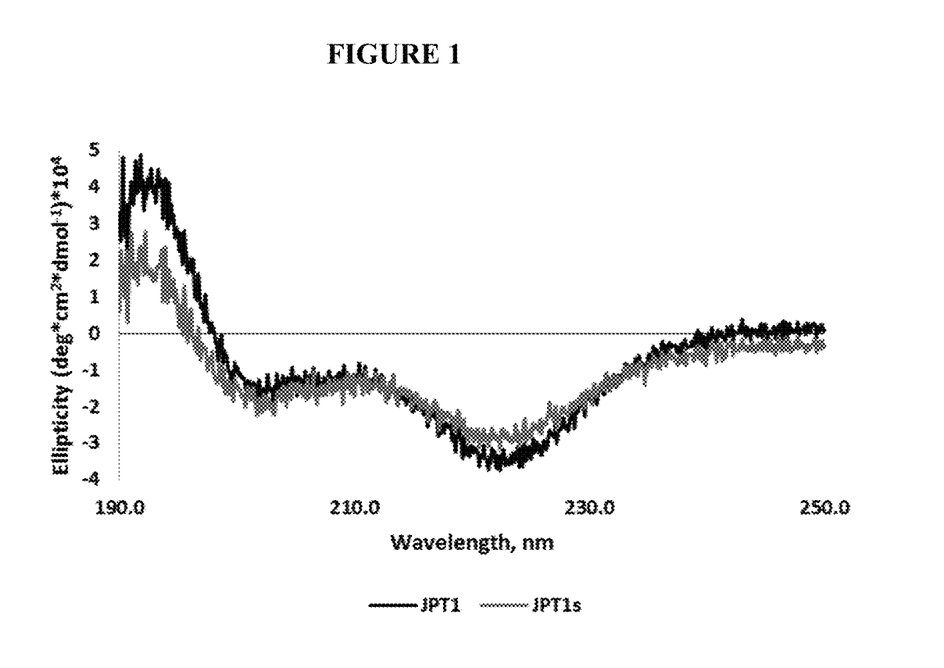
FIG. 1 is a graph showing the Circular dichroism spectra for JPT1 (black) and JPT1s (red). The spectra depict a polyproline type-I-like helical secondary structure.

The impact of placement of aromatic side chains within the peptoid on peptoid-induced modulation of Aβ40 aggregation was evaluated by reordering the JPT1 sequence to create JPT1s (Table 1). Unlike JPT1, JPT1s does not contain aromatic side chains with adjacent placement on the same helical face. In contrast, JPT1s was designed such that two faces of the helix contain only one F-like side chain and one face of the helix contains two F-like side chains located at opposite ends of the helix, ~12 Å apart. JPT1s was shown to have a helical secondary structure in methanol by circular dichroism (FIG. 1).

The importance of peptoid side chain chirality on peptoid-induced modulation of Aβ40 aggregation was investigated by designing a peptoid that maintains the side chain sequence of JPT1 but lacks side chain chirality and therefore helical secondary structure (JPT1a; Table 1). Side chain chemistry was maintained, but achiral side chains (i.e., those that do not contain a methyl group at the α-carbon position) were used in place of the chiral side chains within JPT1 (see structures in Table 1). Circular dichroism was not performed for JPT1a since achiral peptoids exhibit a flat spectrum (i.e., don't absorb at these wavelengths).

3.2. Aggregation Assessed Via ThT Fluorescence

Figure 2:
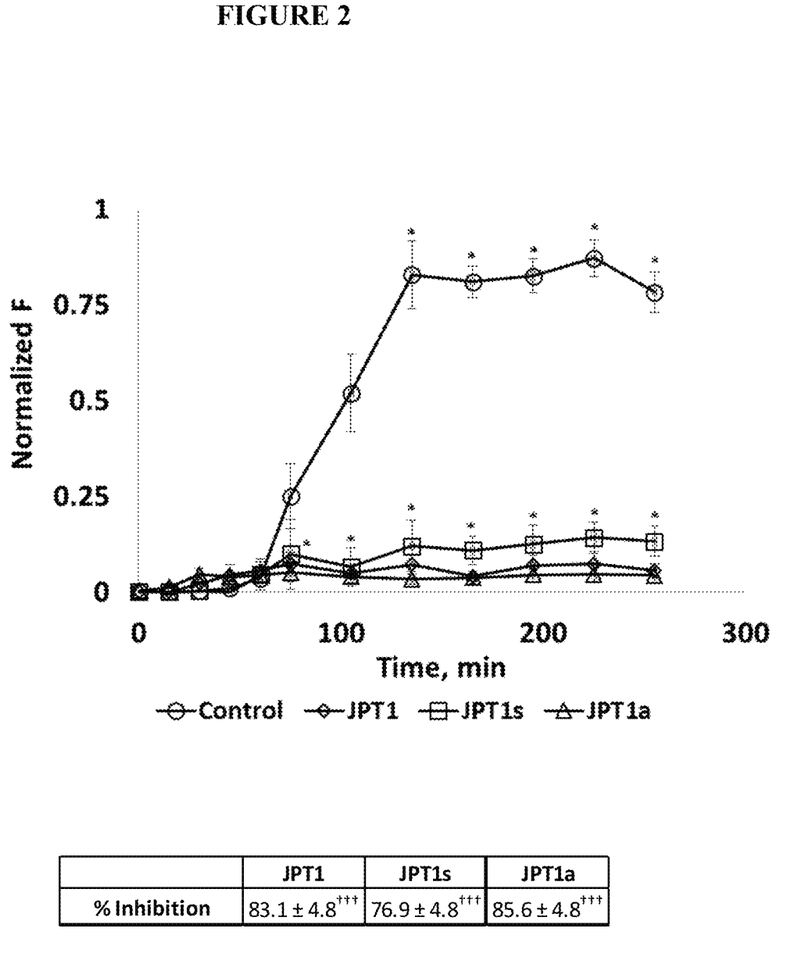
FIG. 2 is a graph and table showing the thioflavin T (ThT) analysis. Peptoid JPT1, JPT1a, and JPT1s modulate Aβ40 aggregation similarly. Peptoids were added to 20 μM Aβ40 monomer at concentrations of 0 (control) or 100 μM, aggregation was initiated via agitation and β-sheet aggregates were detected via ThT fluorescence. Normalized fluorescence values are calculated as a percentage of the control plateau. Parameters are expressed as mean±SEM, n=7. $^{†††}$p<0.0001 vs. control. * indicates data points used for calculation of percent inhibition.

Aggregation assays were performed and monitored via ThT fluorescence to assess the ability of JPT1, JPT1s, and JPT1a to modulate Aβ40 aggregation. ThT is a benzothiazole dye that binds to β-sheet rich amyloid aggregate structures, resulting in a shifted and enhanced fluorescent signal. Hudson et al., FEBS J. 276, 5960-5972 (2009). Aggregations were performed with 20 µM Aβ40 monomer in the absence (control) and presence of 100 µM JPT1, JPT1s, or JPT1a. In the absence of peptoid, Aβ40 aggregation exhibited a lag time (the time at which fluorescence begins to increase) of 60 min, followed by rapid β-sheet accumulation for 75 min, and ending in a plateau, where β-sheet aggregates are in equilibrium with monomer (FIG. 2). These data are in agreement with previous studies of Aβ aggregation.

In the presence of JPT1, the ThT fluorescence plateau at equilibrium was significantly reduced, prohibiting a conclusive determination of the lag time and indicating that fewer β-sheet aggregates were present at equilibrium (FIG. 2). Inhibition of Aβ40 aggregation was 83.1±4.8% in the presence of JPT1, which compares well with our previously reported value of 81.2±4.4%. Similarly, addition of either JPT1s or JPT1a resulted in a pronounced reduction in the ThT fluorescence plateau at equilibrium of 76.9±4.8% and 85.6±4.8%, respectively.

3.3. Aggregation Assessed Via Dot Blot Analysis

To monitor the appearance of fibrillar Aβ40 species, monomer aggregation assays were monitored via immunoblotting with the conformation-specific antibody OC, which recognizes fibrillar aggregates. Pike et al., J Biol Chem 270: 23895-23898 (1995). When Aβ40 was aggregated in the absence of peptoid, dot blot analysis using OC antibody confirms the appearance of fibrillar structures beginning at 45 min (FIG. 3), slightly earlier than that observed with ThT fluorescence (FIG. 2). This difference in lag time is not unexpected since ThT and OC recognize different Aβ40 aggregate conformations. As for ThT fluorescence, the initial lag observed with dot blot analysis is followed by a rapid growth phase and finally a plateau where fibrils are in equilibrium with monomer.

Figure 3:
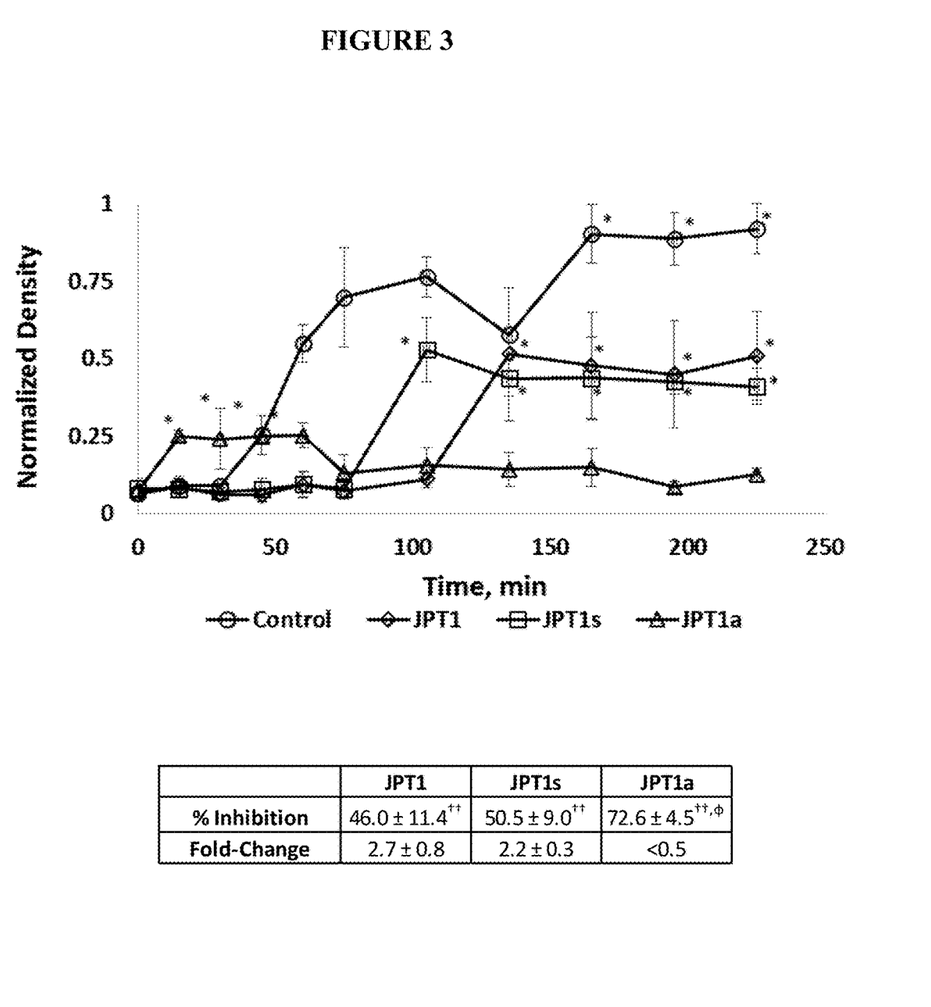

The addition of JPT1, JPT1s, or JPT1a modulated Aβ40 aggregation (FIG. 3). Specifically, JPT1 resulted in a 2.7±0.8 fold increase in lag time versus the control and a 46.0±11.4% decrease in fibrillar aggregates at equilibrium. In our previously published data we observed a <0.31 fold change, or decrease, in lag time compared to the control and a 63.7±9.2% decrease in fibrillar aggregates. While in both cases it is clear that JPT1 has modulated Aβ aggregation, the difference is likely due to the variation in Aβ lots between the studies. Lot-to-lot differences in TFA salt content can greatly affect the quality of monomer preparation as well as the aggregation results.

The addition of JPT1s resulted in a 2.2±0.4 fold increase in lag time versus the control and a 50.5±9.0% reduction of fibrillar aggregates. The presence of JPT1a resulted in a <0.50 fold change, or reduction, in lag time versus the control and a 72.6±4.5% reduction of fibrillar aggregates. Thus, JPT1a was more effective at reducing OC-binding fibrillar aggregates than JPT1 and JPT1s. These results suggest that the lack of side chain chirality in the JPT1a sequence, and therefore increase in flexibility, may improve modulation of Aβ aggregation.

3.4. Morphology Studies

Figure 4:
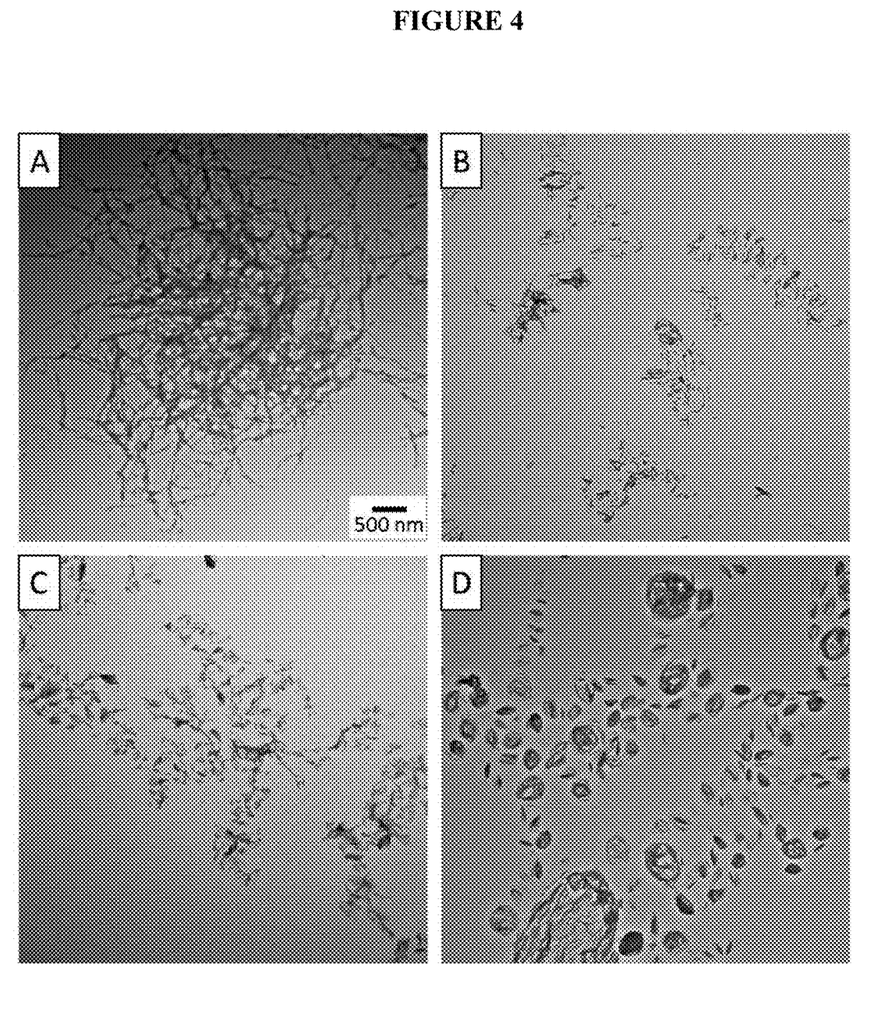
FIG. 4 is a set of photographs showing the morphology of Aβ40 aggregates formed in the absence and presence of peptoids JPT1, JPT1s, and JPT1a with varying side chain placement and helicity. 20 μM Aβ40 monomer in 40 mM Tris-HCl (pH 8.0) was aggregated alone (control, FIG. 4A) or in the presence of 100 μM peptoid (FIG. 4B) JPT1, (FIG. 4C) JPT1s, or (Fig. D) JPT1a. The control reaction was monitored via ThT fluorescence and upon plateau equilibrium was observed, samples were gridded and visualized by TEM at 255 min. Results are representative of 3 independent experiments and imaged grids were randomly selected. Scale bars are 500 nm.

To confirm the inhibition of Aβ40 aggregation in the presence of peptoids and investigate variation in aggregate morphology induced by different peptoid sequences, TEM images were acquired after aggregations reached equilibrium, as observed by ThT fluorescence. In the absence of peptoid, Aβ40 formed thick fibrillar-like aggregates (FIG. 4A), as previously reported. The addition of JPT1, JPT1s, or JPT1a resulted in a reduction in the overall number of aggregates, corresponding to ThT fluorescence and dot blot data (FIGS. 4B-D). While the aggregates formed in the presence of peptoid were all smaller than and lacked the fibrillar branching observed in the control, the morphology and size of Aβ40 aggregates formed in the presence of the different peptoids varied considerably. The addition of JPT1 resulted in small aggregates with no extensive branching (FIG. 4B). Aβ40 aggregates formed in the presence of JPT1s displayed a similar morphology to those formed in the presence of JPT1, but were slightly larger in size (FIG. 4C). In contrast, the addition of JPT1a resulted in Aβ40 aggregates that adopt a circular, bird nest-like morphology (FIG. 4D). While these aggregates also do not exhibit branching, they are larger in size than the aggregates formed in the presence of JPT1.

Figure 5:
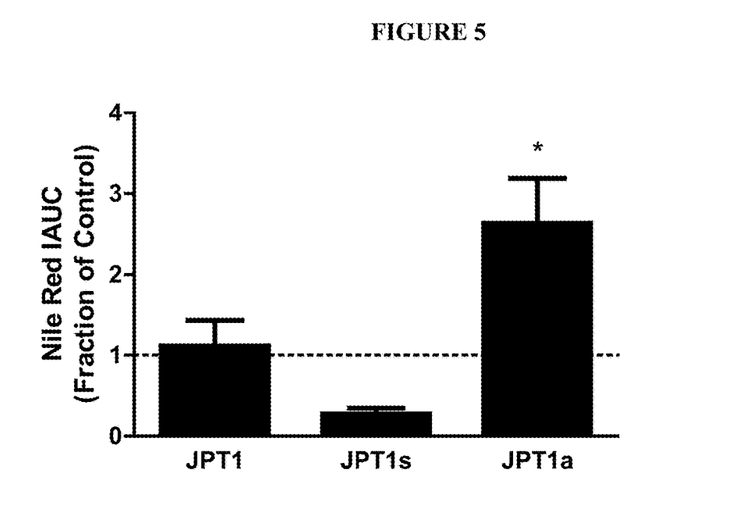
FIG. 5 is a graph showing surface hydrophobicity of Aβ40 aggregates made in the presence of peptoids JPT1, JPT1s, and JPT1a. Aggregation reactions were performed as in FIG. 4. When the equilibrium plateau was reached, samples were combined with 200 μM Nile Red at a 10:1 molar ratio (Nile Red:Aβ). IAUC (580-700 nm) was blank subtracted and normalized to the control. Parameters are expressed as mean±SEM, n=3-4. *p<0.05, assessed via one-way ANOVA.

Nile Red was used to further probe conformational changes of Aβ40 aggregates made in the presence of peptoids. Nile Red, a lipophilic dye, emits increased fluorescence intensity when in the presence of non-polar molecular surfaces, such as hydrophobic residues. See Hawe et al. Pharm Res 25: 1487-1499 (2008) and Yanagi et al., J Biol. Chem 286: 23959-23966 (2011). Thus, differences in Nile Red fluorescence are indicative of aggregate conformational changes. Aβ40 aggregates made in the presence of JPT1a exhibit significantly increased surface hydrophobicity (FIG. 5). In contrast, no significant change in Nile Red fluorescence is observed for aggregates made in the presence of JPT1 and JPT1s. While JPT1s does induce a trend of reduced surface hydrophobicity, this trend does not reach significance. These results confirm the structural changes induced by peptoids, and suggest that JPT1a induces that most pronounced changes in aggregate conformation.

4. Discussion

We have shown that three peptoid-based mimics of the Aβ hydrophobic core (KLVFF) modulate Aβ40 aggregation. All three peptoids, which vary in side chain placement (JPT1 vs. JPT1s) and chirality (JPT1 vs. JPT1a), elicited a similar effect on the formation of ThT-binding β-sheet containing aggregates. However, immunoblotting assays and TEM images suggest that the Aβ40 aggregation pathway is not the same in the presence of the three peptoid sequences.

In order to determine the importance of aromatic side chain placement, the sequence of JPT1 was reordered to create JPT1s, which presents ~12 Å spacing of F-like residues on a single face of the helix as opposed to ~6 Å spacing of F-like residues on two faces. This change in spacing had little effect on the lag time to aggregate formation or the quantity of fibrillar aggregates as observed by ThT and immunoblotting. TEM analysis further confirms that Aβ40 aggregates formed in the presence of JPT1s exhibit similar morphology to those formed in the presence of JPT1, although the aggregates formed in the presence of JPT1s are larger than those formed in the presence of JPT1. These results indicate that the spacing of F-like side chain groups on the face of the helix has a limited effect on the interaction between the peptoid and Aβ.

JPT1a was designed with the same side chain sequence as JPT1, but without chiral centers in the I-like and F-like groups. This lack of side chain chirality prohibits the peptoid from forming a helical secondary structure. This change in side chain chirality led to a more pronounced reduction in both the quantity of fibrillar aggregates and the lag time to aggregate formation, as observed by dot blot assays. In addition, TEM images show that the presence of JPT1a results in Aβ40 aggregates with a unique circular morphology and larger size. This altered morphology likely contains fewer fibrillar structures, which leads to the reduced detection by the fibril-specific antibody OC in dot blot assays. This change in aggregate morphology and altered interaction with Aβ may be due to the ability of peptoids that contain side chains without chiral centers or steric bulk, such as JPT1a, to adopt a trans conformation. The increased likelihood for JPT1a to form a trans conformation would lead to increased backbone flexibility, which may result in improved interaction with Aβ monomer and/or aggregates. The data presented here suggest that the flexible secondary structure of JPT1a induces a different Aβ aggregation pathway that forms unique aggregate morphologies.

Figure 6:
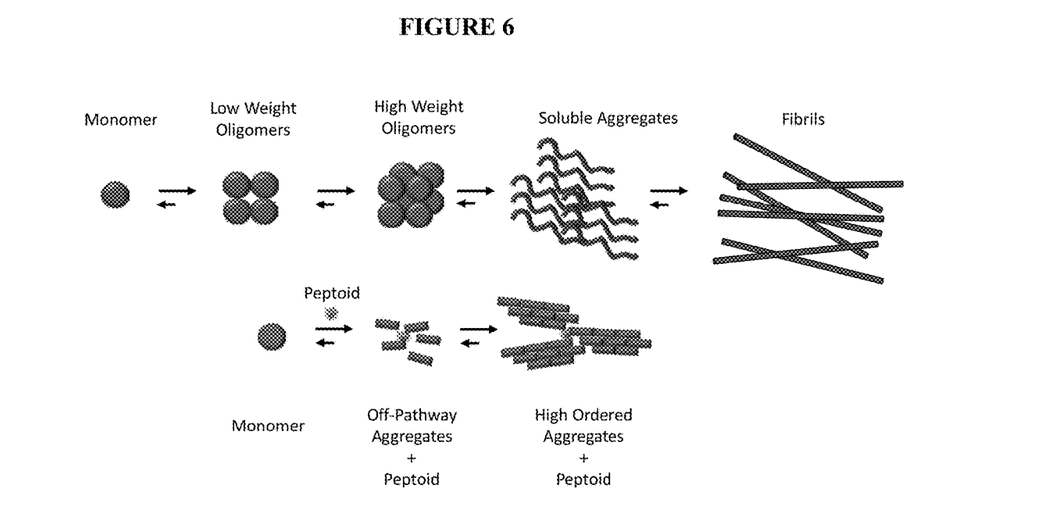
FIG. 6 is a schematic of a proposed mechanistic representation of how peptoids may create off-pathway Aβ higher ordered aggregates. Future work will focus on utilizing atomic force microscopy (AFM) to quantitate the size of early aggregates in the lag phase associated with Aβ aggregation.

These results indicate that peptoids with varying sequences modulate Aβ aggregation. While ThT fluorescence indicates that all peptoids work in a similar manner, immunoblotting and TEM images demonstrate differences in the number and the morphology of Aβ aggregates formed in the presence of the different peptoid sequences. In particular, the lack of chirality in JPT1a led to more effective inhibition of fibrillar aggregate formation, a reduction rather than extension of the lag time to aggregate formation, and a unique aggregate morphology. These results indicate that JPT1a may facilitate the formation of off-pathway higher ordered aggregates of Aβ (FIG. 6), similar to a pathway reported previously when Aβ was aggregated in the presence of "fibrillar seeds". Wu et al., *Biochem. Biophys. Res. Commun.* 439, 321-326 (2013). These fibrillar seeds were shown to propagate fibril formation while significantly reducing both total aggregate levels and soluble oligomer toxicity. The unique ability of JPT1a to induce these changes suggests that cis-trans isomerization may play a key role in the interaction of peptoids with Aβ aggregates.

5. Conclusion

The results of this study provide a better understanding for how peptoids, and therefore other peptides and small molecules, interact with Aβ and its aggregates. Further studies involving peptoid-based mimics of the hydrophobic core of Aβ will elucidate the alternate aggregation pathways that were observed here. This improved understanding of the aggregation pathway will allow for rational design of AD therapeutics.

We claim:

1. A peptoid composition comprising eight peptoid monomers,
wherein the eight peptoid monomers are arranged in consecutive order from the N-terminal end to the C-terminal end and comprise achiral side chain groups $R_1$, $R_2$, $R_3$, $A_1$, $A_2$, X, $A_3$, and $A_4$, respectively,
wherein $R_1$ is selected from an unbranched, terminally substituted $C_2$-$C_5$ aminoalkyl group,
wherein each of $R_2$ and $R_3$ of the peptoid is independently selected from an unbranched, unsubstituted $C_1$-$C_5$ alkyl group;
wherein each of $A_1$, $A_2$, $A_3$, and $A_4$ of the peptoid are independently selected from a $C_6$ aryl or an unbranched $C_7$-$C_8$ arylalkyl group,
wherein X of the peptoid is an unbranched, unsubstituted $C_1$-$C_5$ alkyl group.

2. The peptoid of claim 1, wherein each of $A_1$, $A_2$, $A_3$, and $A_4$ are a phenylmethyl group.

3. The peptoid of claim 1, wherein $R_1$ is a 4-aminobutyl group.

4. The peptoid of claim 1, wherein $R_2$ and $R_3$ are propyl groups.

5. The peptoid of claim 1, wherein X is a propyl group.

6. A pharmaceutical composition comprising the peptoid of claim 1 and a pharmaceutically acceptable carrier.

7. The peptoid of claim 1, wherein each of $A_1$, $A_2$, $A_3$, and $A_4$ are a phenylmethyl group and $R_2$, $R_3$, and X are propyl groups.

8. The peptoid of claim 1, wherein $R_1$ is a 4-aminobutyl group and each of $A_1$, $A_2$, $A_3$, and $A_4$ are a phenylmethyl group.

9. The peptoid of claim 1, wherein $R_1$ is a 4-aminobutyl group and $R_2$, $R_3$, and X are propyl groups.

10. A peptoid of formula

11. A pharmaceutical composition comprising the peptoid of claim 10 and a pharmaceutically acceptable carrier.

12. The peptoid of claim 10, wherein the peptoid is part of a longer peptoid chain.

13. A pharmaceutical composition comprising the peptoid of claim 12 and a pharmaceutically acceptable carrier.

* * * * *

UNITED STATES PATENT AND TRADEMARK OFFICE
CERTIFICATE OF CORRECTION

PATENT NO. : 10,167,315 B2
APPLICATION NO. : 15/191925
DATED : January 1, 2019
INVENTOR(S) : Shannon Servoss et al.

Page 1 of 1

It is certified that error appears in the above-identified patent and that said Letters Patent is hereby corrected as shown below:

In the Specification

Column 1, Lines 8-11 replace with the following:
This invention was made with government support under Grant Numbers P30 RR031154 and P30 GM103450 awarded by the National Institutes of Health. The government has certain rights in this invention.

Signed and Sealed this
Twenty-fourth Day of December, 2019

Andrei Iancu
*Director of the United States Patent and Trademark Office*